US010072009B2

(12) United States Patent
Bharate et al.

(10) Patent No.: US 10,072,009 B2
(45) Date of Patent: Sep. 11, 2018

(54) N-SUBSTITUTED BETA-CARBOLINIUM COMPOUNDS AS POTENT P-GLYCOPROTEIN INDUCERS

(71) Applicant: Council of Scientific and Industrial Research, New Delhi (IN)

(72) Inventors: Sandip Bharate, Jammu-Tavi (IN); Ajay Kumar, Jammu-Tavi (IN); Sudhakar Manda, Jammu-Tavi (IN); Prashant Joshi, Jammu-Tavi (IN); Sonali Bharate, Jammu-Tavi (IN); Ram Vishwakarma, Jammu-Tavi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/521,170

(22) PCT Filed: Oct. 21, 2015

(86) PCT No.: PCT/IN2015/050142
§ 371 (c)(1),
(2) Date: Apr. 21, 2017

(87) PCT Pub. No.: WO2016/063303
PCT Pub. Date: Apr. 28, 2016

(65) Prior Publication Data
US 2017/0334911 A1 Nov. 23, 2017

(30) Foreign Application Priority Data
Oct. 21, 2014 (IN) .............. 3002/DEL/2014

(51) Int. Cl.
*C07D 471/14* (2006.01)
*C07D 471/04* (2006.01)
(52) U.S. Cl.
CPC ......... *C07D 471/14* (2013.01); *C07D 471/04* (2013.01)
(58) Field of Classification Search
CPC .................................... C07D 471/14
See application file for complete search history.

(56) References Cited

FOREIGN PATENT DOCUMENTS

WO    WO-2016063303    4/2016

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*

Bharate, S. B., "Chemistry and Biology of Fascaplysin, a Potent Marine-Derived CDK-4 Inhibitor", Mini-Reviews in Medicinal Chemistry, 12(7), 2012. 650-664, (2012), 650-664.
Bharate, Sandip B., et al., "Total synthesis and anti-cholinesterase activity of marine-derived bis-indole alkaloid fascaplysin", Med. Chem. Commun., 2012,3, 1098-1103, (Jun. 18, 2012), 1098-1103.
Pearce, H. L., et al., "Structural characteristics of compounds that modulate P-glycoprotein-associated multidrug resistance", Advances in Enzyme Regulation, vol. 30, 1990, pp. 357-373, (1990), 357-373.
Roll, Deborah M., et al., "Fascaplysin, an unusual antimicrobial pigment from the marine sponge *Fascaplysinopsis* sp", J. Org. Chem., 1988, 53 (14), pp. 3276-3278, (Jul. 1988), 3276-3278.
Segraves, Nathaniel L., et al., "Comparison of Fascaplysin and Related Alkaloids:? A Study of Structures, Cytotoxicities, and Sources", J. Nat. Prod., 2004, 67 (5), pp. 783-792, (Apr. 10, 2004), 783-792.

(Continued)

*Primary Examiner* — Shawquia Jackson
(74) *Attorney, Agent, or Firm* — Schwegman Lundberg & Woessner, P.A.

(57) ABSTRACT

The present invention relates to the N-substituted beta-carbolinium compounds of general formula A and formulae I and II wherein, $R_1$ and $R_2$ groups are selected from halogens or trifluoromethyl; $R_3$ group is selected from hydrogen or methyl; Ar is selected from aryl and heteroaryl, X is selected from halogens; and $R_1$ and $R_2$ groups may be attached to any position on ring E. The present invention particularly relates to synthesis and p-glycoprotein induction activity of the N-substituted beta-carbolinium compounds. In addition, the invention relates to methods of using compounds for treating or preventing Alzheimer's disease.

General Formula A

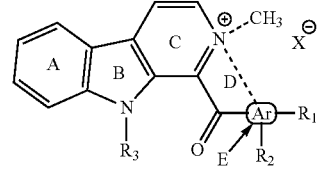

Formulea I and II

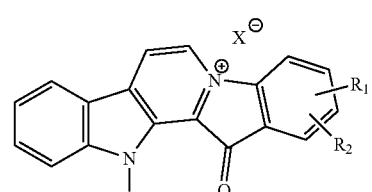

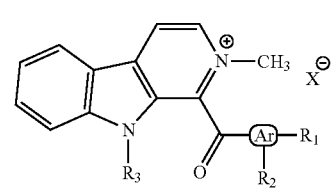

9 Claims, 4 Drawing Sheets

(56) References Cited

OTHER PUBLICATIONS

Soni, R., et al., "Selective in vivo and in vitro effects of a small molecule inhibitor of cyclin-dependent kinase 4", J Natl Cancer Inst. Mar. 21, 2001;93(6):436-46, (Mar. 21, 2001), 436-46.

Soni, Rajeev, et al., "Inhibition of Cyclin-Dependent Kinase 4 (Cdk4) by Fascaplysin, a Marine Natural Product", Biochemical and Biophysical Research Communications, vol. 275, Issue 3, Sep. 7, 2000, pp. 877-884, (Sep. 7, 2000), 877-884.

Soni, Rajeev, et al., "Novel Cdk Inhibitors Restore TGF-β Sensitivity in Cdk4 Overexpressing Epithelial Cells", Biochemical and Biophysical Research Communications, vol. 272, Issue 3, Jun. 16, 2000, pp. 794-800, (Jun. 16, 2000), 794-800.

Zhidkov, Maxim E., et al., "The first syntheses of 3-bromofascaplysin, 10-bromofascaplysin and 3,10-dibromofascaplysin—marine alkaloids from *Fascaplysinopsis reticulata* and *Didemnum* sp. by application of a simple and effective approach to the pyrido[1,2-a:3,4-b']diindole system", Tetrahedron Letters, vol. 48, Issue 45, Nov. 5, 2007, pp. 7998-8000, (Nov. 5, 2007), 7998-8000.

"International Application No. PCT/IN2015/050142, Article 19 amendments filed Mar. 29, 2016", (Mar. 29, 2016), 11 pgs.

"International Application No. PCT/IN2015/050142, International Search Report and Written Opinion dated Jan. 29, 2016", (Jan. 29, 2016), 8 pgs.

Cirrito, John R., "P-glycoprotein deficiency at the blood-brain barrier increases amyloid-β deposition in an Alzheimer disease mouse model", The Journal of Clinical Investigation, vol. 115 (11), Nov. 2005, (Nov. 2005), 3285-3290.

Lam, Fred C., et al., "β-Amyloid efflux medicated by p-glycoprotein", Journal of Neurochemistry, 2001, 76, 1121-1128, (2001), 1121-1128.

Lu, X. L., et al., "Anti-proliferation of human cervical cancer HeLa cell line by fascaplysin through apoptosis induction", Yao Xue Xue Bao, Sep. 2009; 44(9); 980-6 [abstract only; article in Chinese], (Sep. 2009), 980-986.

Mawuenyega, Kwasi G., et al., "Decreased Clearance of CNS Amyloid-β in Alzheimer's Disease", Science, Dec. 24, 2010 ; 330 (6012): 1774, (Dec. 24, 2010), 4 pgs.

Segraves, Nathaniel L., et al., "Structures and cytotoxicities of fascaplysin and related alkaloids from two marine phyla—Fascaplysinopsis sponges and Didemnum tunicates", Tetrahedron Letters 44 (2003) 3471-3475, (Mar. 11, 2003), 3471-3475.

\* cited by examiner

N-SUBSTITUTED BETA-CARBOLINIUM COMPOUNDS AS POTENT P-GLYCOPROTEIN INDUCERS

PRIORITY CLAIM TO RELATED APPLICATIONS

This application is a U.S. national stage application filed under 35 U.S.C. § 371 from International Application Serial No. PCT/IN2015/050142, which was filed 21 Oct. 2015, and published as WO2016/063303 on 28 Apr. 2016, and which claims priority to India Application No. 3002/DEL/2014, filed 21 Oct. 2014, which applications and publication are incorporated by reference as if reproduced herein and made a part hereof in their entirety, and the benefit of priority of each of which is claimed herein.

FIELD OF THE INVENTION

The present invention relates to N-substituted beta-carbolinium compounds as potent P-glycoprotein inducers. More particularly, the present invention relates to methods for the treatment of Alzheimer's disease, including those caused by deposition of amyloid-β plaques inside nerve cells. Compounds of the present invention can be used for the prevention or in the treatment of Alzheimer's disease.

BACKGROUND OF THE INVENTION & DESCRIPTION OF PRIOR ART

Alzheimer's disease is the most common form of senile dementia and the fourth highest cause of disability and death in the elderly. It is characterized by the presence of three main brain hallmarks viz. diffuse neuronal loss with a particular involvement of the cholinergic system, extracellular protein deposits (amyloid plaques) and intracellular protein deposits (neurofibrillary tangles, NFTs). All current therapies are based on the cholinergic hypothesis and demonstrate only symptomatic treatment. Progression of the disease is not slowed or halted, with symptoms continuing to deteriorate over time. The amyloid hypothesis proposes that Alzheimer's disease is caused by an imbalance between Amyloid β production and clearance, resulting in increased amounts of Amyloid β in various forms such as monomers, oligomers, insoluble fibrils and plaques in the CNS. The rate of Amyloid β production is same as that in healthy volunteers; whereas rate of clearance is impaired by 25-30%. High levels of Amyloid β then initiate cascade of events culminating in neuronal damage and death manifesting as progressive dementia of the Alzheimer's disease type. Evidence shows that insufficient clearance of the Amyloid β protein is a prime cause in over 95% of Alzheimer's disease patients (Mawuenyega, K. G. et al. *Science* 2010, 330, 1774). Further it is known that Amyloid β efflux is mediated by p-glycoprotein efflux pump. The p-glycoprotein deficiency at the blood-brain barrier increases Amyloid β deposition in an Alzheimer's disease (Cirrito, J. R. et al., *J. Clin. Invest.* 2005, 115, 3285). P-glycoprotein (P-glycoprotein) is highly expressed on the luminal surface of brain capillary endothelial cells and contributes to the BBB. In P-glycoprotein-null mice, [$^{125}$I]-Amyloid β40 and [$^{125}$I]-Amyloid β42 microinjected into the CNS clear at half the rate that they do in WT mice. When amyloid precursor protein-transgenic (APP-transgenic) mice were administered a P-glycoprotein inhibitor, Amyloid β levels within the brain interstitial fluid significantly increased within hours of treatment. APP-transgenic, P-glycoprotein-null mice had increased levels of brain Amyloid β and enhanced Amyloid β deposition compared with APP-transgenic, P-glycoprotein WT mice. These data establish a direct link between P-glycoprotein and Amyloid β metabolism in vivo and suggest that P-glycoprotein activity at the BBB could affect risk for developing Alzheimer's disease as well as provide a novel diagnostic and therapeutic target (Lam, F. C. et al., *J. Neurochem.* 2001, 76, 1121). Thus it is evident that drugs that have ability to increase levels of P-glycoprotein should increase amyloid clearance. Fascaplysin (1) is a fused benzoyl-linked beta-carbolinium alkaloid isolated from marine sponge Fascaplysinopsis Bergquist sp. collected in the South Pacific near the Fiji Island as an unusual antimicrobial pigment (Roll, D. M. et al., *J. Org. Chem.* 1988, 53, 3276). It showed inhibition of the growth of several microbes, including *Staphylococcus aureus, Escherichia coli, Candida albicans*, and *Saccharomyces cerevisiae*. It showed suppression in the proliferation of mouse leukemia cells L-1210 with $ED_{50}$=0.2 μM (Roll, D. M. et al., *J. Org. Chem.* 1988, 53, 3276) and also exhibited selectivity in murine tumor cytotoxicity assay (Segraves, N. L. et al., *Tetrahedron Lett.* 2003, 44, 3471). Fascaplysin exhibited anti-proliferation effect towards human cervical cancer HeLa cells through induction of apoptosis via extrinsic death pathway and mitochondrial pathway, but not arresting cell cycle progression at G1 phase (Lu, X. et al., *Yaoxue Xuebao* 2009, 44, 980). Fascaplysin showed promising specific CDK-4 inhibitory activity with $IC_{50}$ of 0.35 μM and it also blocked the growth of cancer cells at the G0/G1 phase of the cell cycle (Soni, R. et al., *Biochem. Biophys. Res. Commun.* 2000, 275, 877; Segraves, N. L. et al., *J. Nat. Prod.* 2004, 67, 783; Soni, R. et al., *Biochem. Biophys. Res. Commun.* 2000, 272, 794; Soni, R. et al., *J. Natl. Cancer Inst.* 2001, 93, 436; for review, see: Bharate, S. B. et al., *Mini-Rev. Med. Chem.* 2012, 12, 650). Fascaplysin also displayed inhibition of acetylcholinesterase (AChE) with $IC_{50}$ value of 1.49 μM (Bharate, S. B. et al., *Med. Chem. Commun.* 2012, 3, 1098).

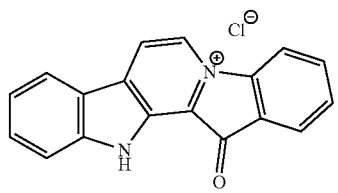

1

OBJECTIVES OF THE INVENTION

The main object of the present invention is to provide a N-substituted beta-carbolinium compounds for P-glycoprotein induction activity.

Still another object of the present invention is to provide a N-substituted beta-carbolinium compounds for treating Alzheimer's disease.

SUMMARY OF THE INVENTION

Accordingly, the present invention provides a compound represented by the general formula A General formula A

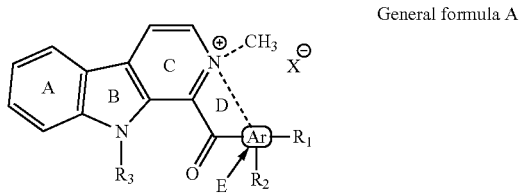

wherein, the case D ring may be cyclized or in open form. when D ring is cyclized, the dotted line indicates single bond connected from ortho-position of aromatic ring E (Ar) to the nitrogen atom of ring C; making five-membered ring. In this case, another dotted bond shown on nitrogen of C ring is not present, when D ring is open, the dotted line connecting aromatic ring E (Ar) to the nitrogen atom of ring C indicates no bond. In this case, another dotted bond shown on nitrogen of ring C indicates presence of single bond connecting nitrogen atom to the methyl group, wherein, $R_1$ and $R_2$ groups are selected from halogens or trifluoromethyl; $R_3$ group is selected from hydrogen or methyl; X is selected from halogens; and Ar is selected from aryl and heteroaryl, $R_1$ and $R_2$ groups may be attached to any position on ring E.

In another embodiment of the present invention, a compound is represented by the formulae I and II.

Formulae I and II

I

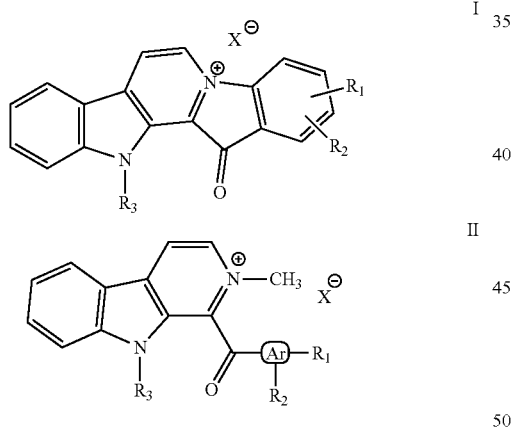

II wherein, $R_1$ and $R_2$ groups are selected from halogens or trifluoromethyl; $R_3$ group is selected from hydrogen or methyl; X is selected from halogens; and Ar is selected from aryl and heteroaryl. wherein, $R_1$ and $R_2$ groups may be attached to any position of aryl or heteroaryl ring.

I

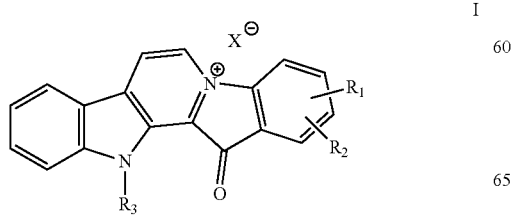

II

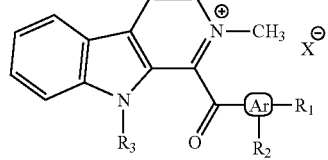

In another embodiment of the invention, the representative compounds comprising the structural formulae:

2

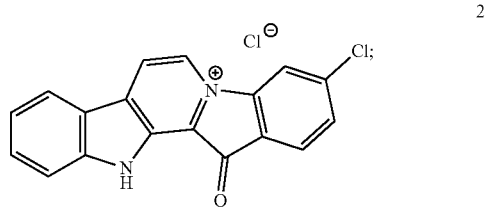

3

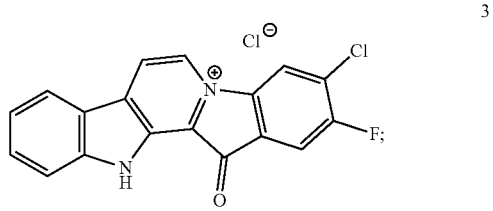

4

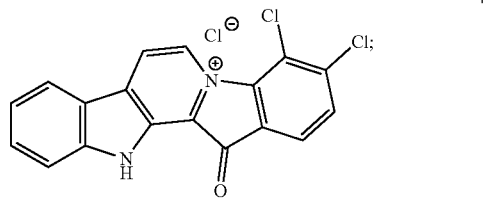

5

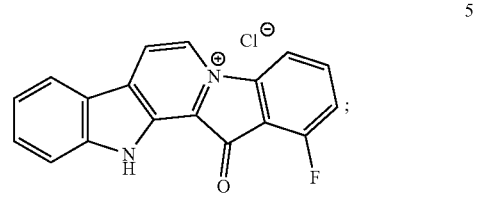

6

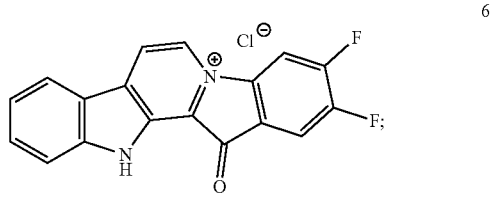

7

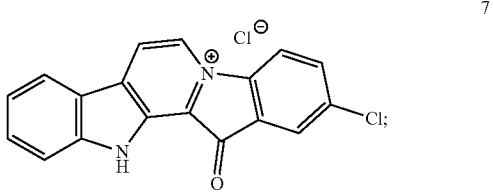

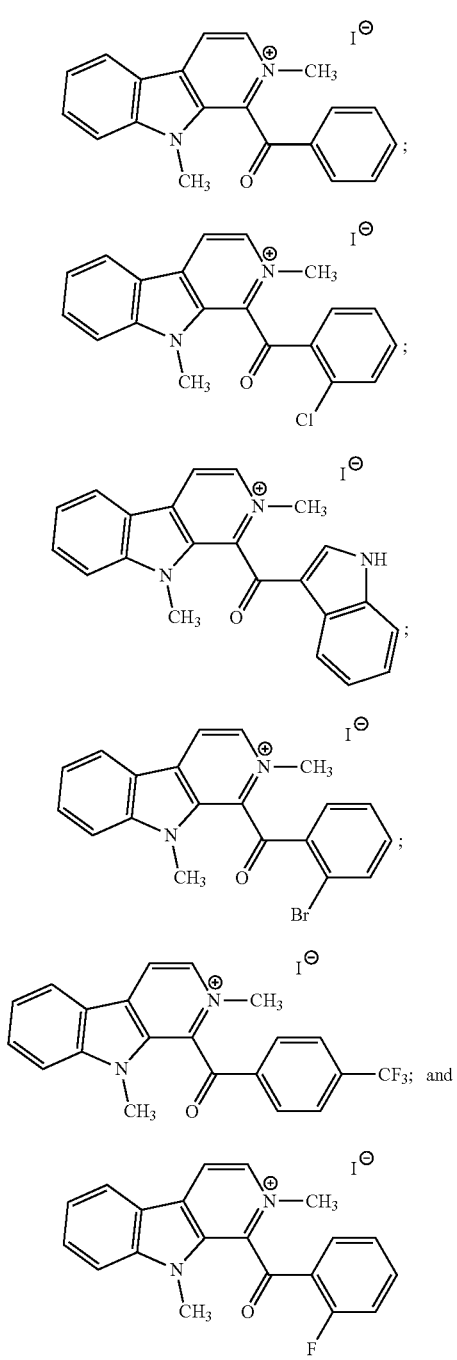

In another embodiment of the present invention, the above described compounds are useful for the treatment of Alzheimer's disease.

In one more embodiment of the present invention, compounds 6 and 11 displayed $EC_{50}$ of 2.0 and 3.0 nM respectively.

A process for the preparation of the beta-carbolinium compounds (1-13), wherein the process steps comprising;

a. reacting tryptamine (35) and substituted glyoxal (21-27 and 36-40) in glacial acetic acid in presence of Pd/C catalyst at reflux temperature over a period of time ranging between 3 to 4 h, b. filtering the reaction mixture through filter paper to obtain filtrate and the filtrate was concentrated on rotary evaporator to get crude product which on silica gel column chromatography (10 to 20% ethyl acetate in hexane) gave substituted benzoylated beta-carboline (28-34 and 41-45), c. heating the substituted benzoylated beta carboline (28-34) obtained as obtained in step (b) at a temperature ranging between 220-230° C. for a period of time between 15-20 minutes leads to cyclized beta carbolinium compounds, recrystallized from DCM/diethyl ether to obtain pure compound (1-7), d. reacting substituted benzoylated beta carbolines (29 and 41-45,) with the methyl iodide in DMF for a period of time ranging between 10 to 12 h at temperature ranging between 80 to 90° C. in sealed tube, cooling of reaction mixture and recrystallization of reaction mixture from DCM provided pure compound (8-13).

In another embodiment of the present invention, a pharmaceutical composition for the treatment of Alzheimer's disease comprising; an effective amount of the compound of general formula A optionally along with the pharmaceutically acceptable excipients, diluents.

In another embodiment of the present invention wherein a pharmaceutical composition for the treatment of Alzheimer's disease comprising; an effective amount of the compound of formulae I and II optionally along with the pharmaceutically acceptable excipients, diluents.

In another embodiment of the present invention, wherein the pharmaceutically acceptable excipient is selected from a group consisting of saccharides (such as lactose, starch, dextrose), stearates (such as stearic acid, magnesium stearate), polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates (such as sodium carbonate, sodium bicarbonate), talc.

LIST OF ABBREVIATIONS

Pgp: P-glycoprotein; BBB: Blood-brain barrier; PBS: Phosphate buffer saline; SGF: Simulated gastric fluid; SIF: Simulated intestinal fluid; NFTs: Neurofibrillary tangles; CNS: Central Nervous System; AChE: acetylcholinesterase; CDK: Cyclin-dependent kinase.

DETAILED DESCRIPTION OF THE INVENTION

The present invention discloses a N-substituted beta-carbolinium compounds represented by the general formula A and formulae I and II as promising P-glycoprotein inducers.

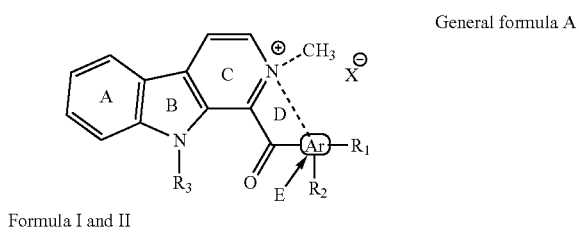

Formula I and II

General formula A

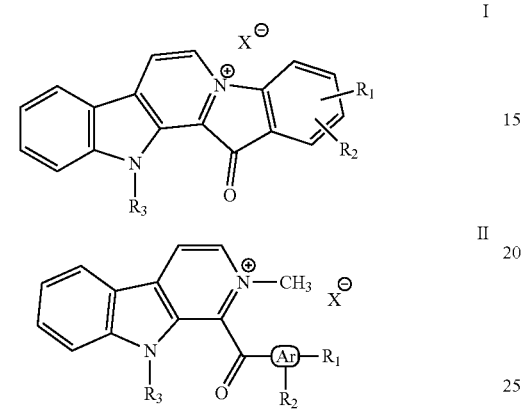

Figure 1:
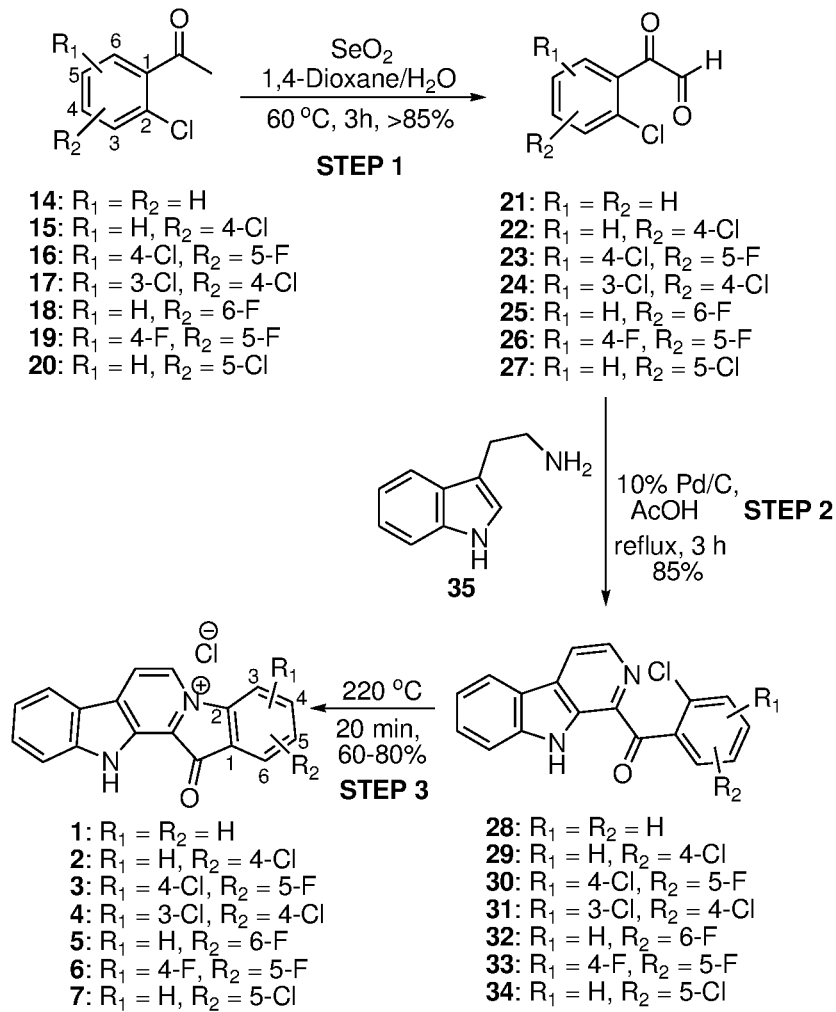
FIG. 1 is a diagram illustrating the chemical synthesis of N-substituted beta-carbolinium compounds 1-7 claimed in the invention.
Figure 2:
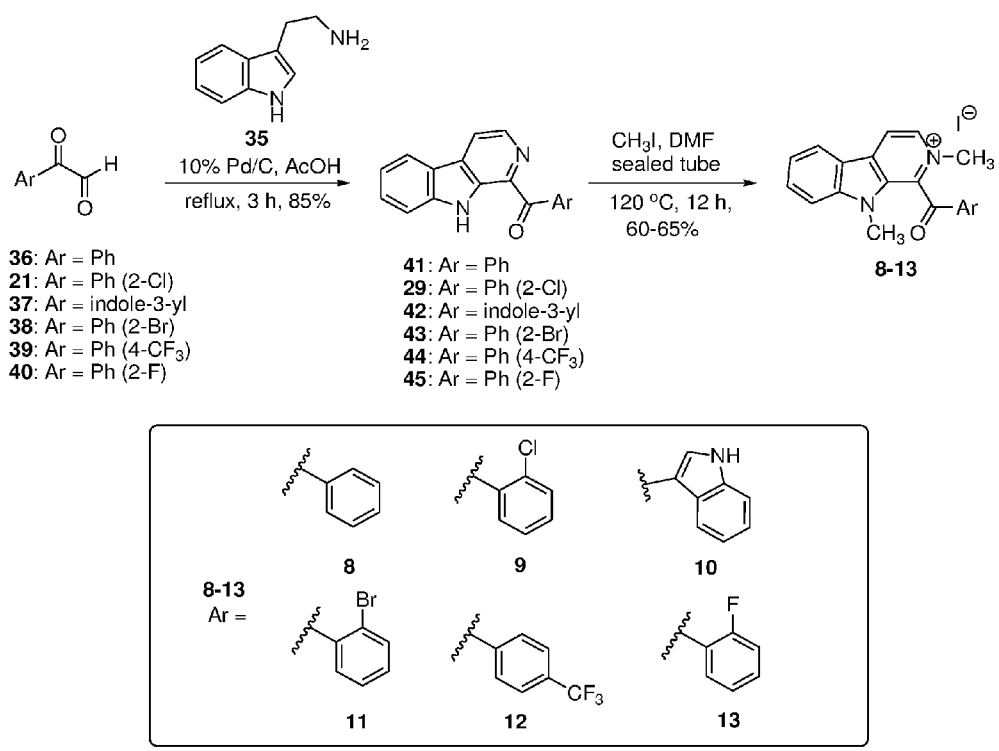
FIG. 2 is a diagram illustrating the chemical synthesis of N-substituted beta-carbolinium compounds 8-13 claimed in the invention.

The present invention relates to a novel N-substituted beta-carbolinium compounds (synthesis shown in FIG. 1 and FIG. 2) that showed promising P-glycoprotein inducing activity. The results of Pgp induction activity of compounds 2-13 are depicted in Table 1.

Figure 3:
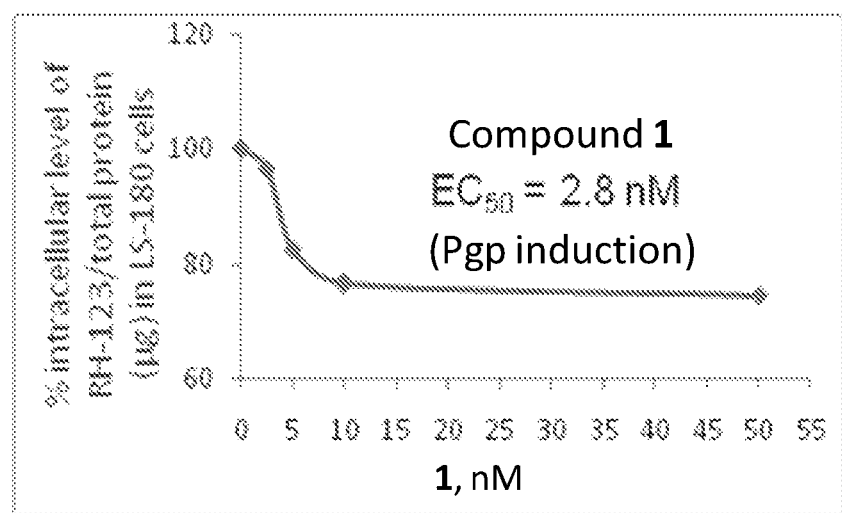
FIG. 3 is a diagram illustrating the P-glycoprotein induction activity of N-substituted beta-carbolinium compound 1 at different concentrations.
Figure 4:
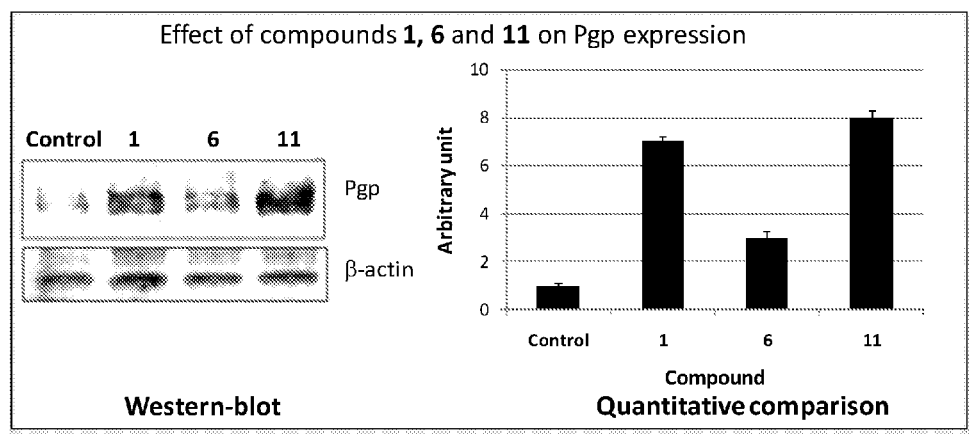
FIG. 4. P-glycoprotein Western-blot analysis of 1, 6 and 11. Quantitiave comparison is also shown.

Results indicated that both fused 2-7 as well as open ring compounds 8-13 displayed Pgp-induction activity. Compound 1 displayed potent induction of p-glycoprotein expression with $EC_{50}$ value of 2.8 nM (FIG. 3). The compound 6 and 11 also displayed Pgp induction with $EC_{50}$ values of 2.0 and 3.0 nM, respectively. The P-glycoprotein induction activity of these compounds was further confirmed by western-blot analysis. The Western-blot results (FIG. 4) clearly indicated that N-substituted beta-carbolinium compound 11 induces P-glycoprotein expression significantly. FIG. 4 also it indicated that compound 11 possess better Pgp induction activity than fascaplysin (1). The promising Pgp induction activity of these compounds indicates their potential to develop as Anti-Alzheimer agents. Furthermore, these compounds displayed optimum aqueous solubility (Table 3).

A class of N-substituted beta-carbolinium compounds is presented and defined by the general formula A:

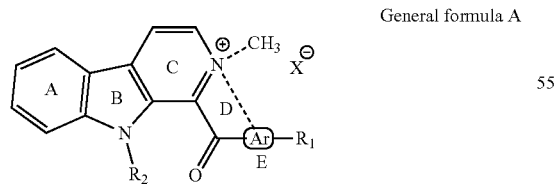

General formula A wherein, D ring may be cyclized or in open form, when D ring is cyclized, the dotted line indicates single bond connected from ortho-position of aromatic ring E (Ar) to the nitrogen atom of ring C; making five-membered ring. In this case, another dotted bond shown on nitrogen of C ring is not present, when D ring is open, the dotted line connecting aromatic ring E (Ar) to the nitrogen atom of ring C indicates no bond. In this case, another dotted bond shown on nitrogen of ring C indicates presence of single bond connecting nitrogen atom to the methyl group, wherein, $R_1$ and $R_2$ groups are selected from halogens or trifluoromethyl; $R_3$ group is selected from hydrogen or methyl; X is selected from halogens; and Ar is selected from aryl and heteroaryl, $R_1$ and $R_2$ groups may be attached to any position on ring E.

A class of N-substituted beta-carbolinium compounds is presented and defined by the formula I and II

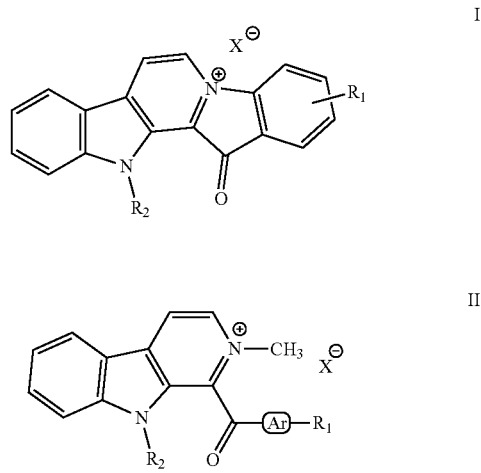

wherein, $R_1$ and $R_2$ groups are selected from group consisting of halogens or trifluoromethyl; $R_3$ group is selected from group consisting of hydrogen or methyl; X is selected from halogens; and Ar is selected from aryl and heteroaryl.

$R_1$ and $R_2$ groups may be attached to any position on aryl or heteroaryl ring E.

Compounds of the invention derived from formula I and II include, but are not limited to, the following chemical structures:

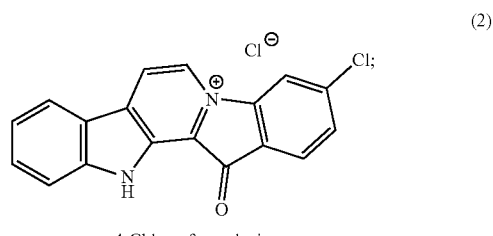

4-Chloro-fascaplysin

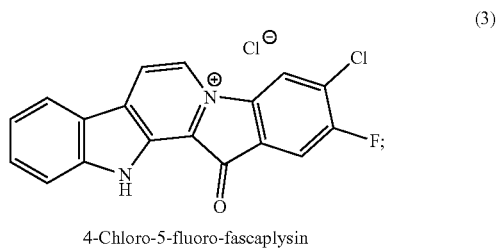

4-Chloro-5-fluoro-fascaplysin

-continued (4)

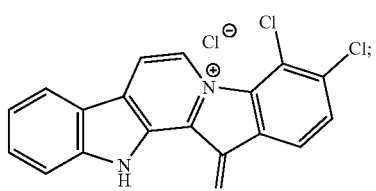

3,4-Dichloro-fascaplysin (5)

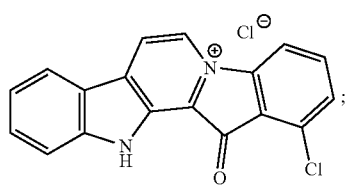

6-Chloro-fascaplysin (6)

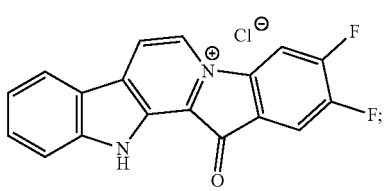

4,5-Difluoro-fascaplysin (7)

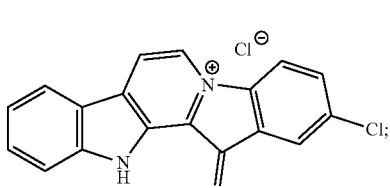

5-Chloro-fascaplysin (8)

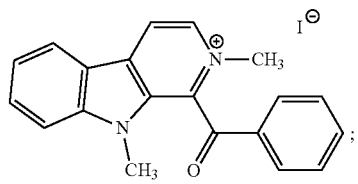

1-Benzoyl-9,2-dimethyl beta-carbolinium iodide (9)

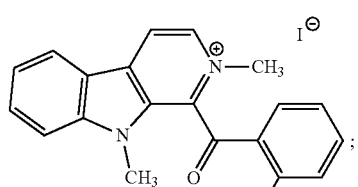

1-(2-Chloro-benzoyl)-9,2-dimethyl beta-carbolinium iodide

-continued (10)

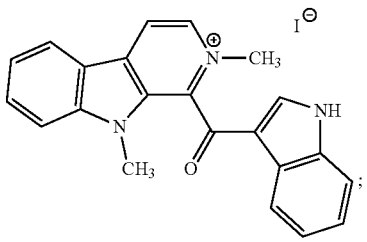

1-(3-Indoloyl)-9,2-dimethyl beta-carbolinium iodide (11)

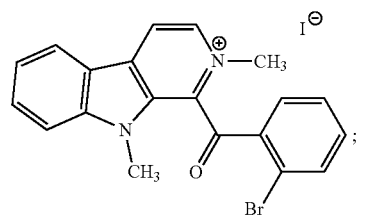

1-(2-Bromo-benzoyl)-9,2-dimethyl beta-carbolinium iodide (12)

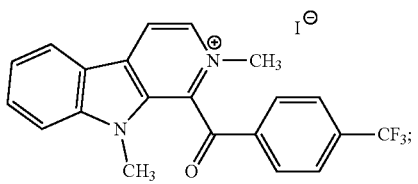

1-(4-Trifluoromethyl-benzoyl)-9,2-dimethyl beta-carbolinium iodide (13)

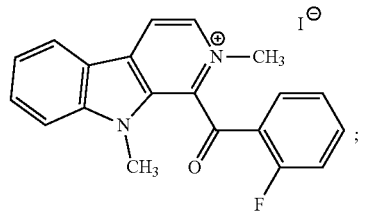

1-(2-Fluoro-benzoyl)-9,2-dimethyl beta-carbolinium iodide

As used herein, the terms below have the meanings indicated.

The term aryl as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The term halo, or halogen, as used herein, alone or in combination, refers to fluorine, chlorine, bromine, or iodine.

The term heteroaryl as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsincludecarbazolyl, benzidolyl, phenanthrolinyl, dibenzofuranyl, acridinyl, phenanthridinyl, xanthenyl and the like.

The compounds of the invention can be used to treat a patient (e.g. a human) that suffers from or is at a risk of suffering from a disease, disorder, condition, or symptom described herein. The compounds of the invention can be used alone or in combination with other agents and compounds in methods of treating or preventing Alzheimer's disease. Each such treatment described above includes the step of administering to a patient in need thereof a therapeutically effective amount of the compound of the invention described herein to delay, reduce or prevent such a disease, disorder, condition, or symptom.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

The following examples are given by way of illustration of the working of the invention in actual practice and should not be construed to limit the scope of the present invention in any way Example 1

Step 1: Synthesis of 2-chlorophenyl glyoxal (21). The solution of $SeO_2$ (1.42 g, 12.79 mmol) in 1,4-dioxane/water (10 mL, 95:5) was heated at 60° C. for 3 h. 2-Chloroacetophenone (14) (2 g, 12.98 mmol) was added and the reaction mixture was refluxed for 4 h. Reaction mixture was filtered and the filtrate was concentrated. The formation of glyoxal was confirmed by TLC and MS. The crude product i.e. 2-chlorophenyl glyoxal (21, 1.84 g, >85% pure) was directly used for the next step without purification. All other glyoxals 22-27 were also prepared using similar procedure.

Step 2: Procedure for Synthesis of 1-(2-chloro benzoyl)-beta-carboline 28. To the solution of tryptamine (35, Purchased from Sigma-Aldrich, cat no. T2891; 1 g, 6.25 mmol) and 2-chlorophenyl glyoxal (21, 1.26 g, 7.5 mmol) in glacial acetic acid (15 mL) was added 10% Pd/C catalyst (20 mol %) and reaction mixture was refluxed for 3 h. Reaction mixture was filtered through Whatman filter paper and the filtrate was concentrated on rotary evaporator to get crude product which on silica gel column chromatography (20% ethyl acetate/hexane) gave β-carboline 28 (1.62 g, 85% yield). Yellow solid; m.p. 203-205° C.; $^1$H NMR (500 MHz CDCl$_3$): δ 10.42 (brs, NH, 1H), 8.56 (d, J=4.8 Hz, 1H), 8.20-8.15 (m, 2H), 7.66-7.59 (m, 3H), 7.53-7.35 (m, 4H); IR (CHCl$_3$): $v_{max}$ 3421, 3058, 2360, 2340, 2360, 1699, 1646, 1626, 1592, 1430, 1212, cm$^{-1}$; ESI-MS: m/z 307.06 [M+H]$^+$; HRMS: m/z 307.0619 calcd for $C_{18}H_{110}IN_2O+H^+$ (307.0632). All other β-carbolines 29-34 and 41-45 were also prepared using similar procedure.

Step 3: Synthesis of Fascaplysin (1). The β-carboline 28 (50 mg, 0.163 mmol) was heated at 220° C. for 15 min Reaction was cooled and the product was recrystallized from CH$_2$Cl$_2$/diethyl ether producing brick-red colored powder of fascaplysin (1, 40 mg) in 80% yield. Brick red solid; m.p. 230-232° C.; $^1$H NMR (500 MHz, CD$_3$OD, ppm): δ 9.40 (d, J=5.6 Hz, 1H), 8.98 (d, J=5.8 Hz, 1H), 8.48 (d, J=7.9, 1H), 8.35 (d, J=8.0 Hz, 1H), 8.08 (d, J=7.3 Hz, 1H), 7.96 (t, J=7.7 Hz, 1H), 7.89 (t, J=7.7 Hz, 1H), 7.79 (d, J=8.3 Hz, 1H), 7.73 (t, J=7.4 Hz, 1H), 7.54 (t, J=7.4 Hz, 1H); $^{13}$C NMR (100 MHz, CD$_3$OD, ppm): δ 183.2 (CO), 148.9 (C), 148.7 (C), 142.9 (C), 138.3 (CH), 135.9 (CH), 133.1 (C), 132.7 (CH), 127.6 (CH), 126.8 (CH), 125.5 (C), 125.2 (CH), 124.6 (CH), 123.6 (C), 121.2 (C), 121.1 (CH), 116.5 (CH), 114.6 (CH); IR (CHCl$_3$): $v_{max}$ 3368, 2923, 2359, 1621, 1506, 1046 cm$^{-1}$; ESI-MS: m/z 271.09 [M−Cl]$^+$; HRMS: m/z 271.0843 calcd for $C_{18}H_{11}N_2O^+$ (271.0866).

Example 2

Synthesis of 4-chloro-fascaplysin (2). Procedure of synthesis is similar to example number 1 (step 1, 2, and 3) except the respective starting material 2,4-dichloro acetophenone is used in step 1. Brick red solid; yield 62%; $^1$HNMR (CD$_3$OD, 400 MHz): δ 9.27 (d, 1H, J=6.4 Hz), 8.88 (d, 1H, J=6 Hz), 8.45 (s, 1H), 8.40 (d, 1H, J=8 Hz), 7.94 (d, 1H, J=8 Hz), 7.82 (t, 1H, J=8 Hz), 7.74-7.68 (m, 2H), 7.46 (t, 1H, J=7.2 Hz); $^{13}$C NMR (100 MHz, CD$_3$OD, ppm): δ 182.0 (C), 149.73 (C), 149.0 (C), 144.2 (C), 143.2 (C), 136.1 (CH), 133.0 (C), 132.7 (CH), 127.9 (CH), 127.7 (CH), 125.3 (CH), 124.7 (C0, 124.2 (CH), 121.2 (C), 121.1 (CH), 117.6 (CH), 1147 (CH); IR (KBr): $v_{max}$ 3468, 2925, 1637, 1418, 1021 cm$^{-1}$; MS (Q-TOF): m/z 305 [M−Cl]$^+$; HRMS: m/z 305.0475 calcd for $C_{18}H_{10}ClN_2O^+$ (305.0476).

Example 3

Synthesis of 4-chloro-5-fluoro-fascaplysin (3). Procedure of synthesis is similar to example number 1 (step 1, 2, and 3) except the respective starting material 2,4-dichloro, 5-fluoro acetophenone is used in step 1. Brick red solid; yield 60%; $^1$H NMR (CD$_3$OD, 400 MHz): δ 9.25 (s, 1H), 8.88 (s, 1H), 8.60 (d, 1H, J=4 Hz), 8.43-8.41 (m, 1H), 7.81-7.72 (m, 3H), 7.49-7.45 (t, 1H, J=8 Hz); IR (KBr): $v_{max}$ 3459, 2925, 1619, 1469, 1048 cm$^{-1}$; MS (Q-TOF): m/z 322.9 [M−Cl]$^+$; HRMS: m/z 323.0379 calcd for $C_{18}H_9ClFN_2O^+$ (323.0382).

Example 4

Synthesis of 3,4-dichloro-fascaplysin (4). Procedure of synthesis is similar to example number 1 (step 1, 2, and 3) except the respective starting material 2,3,4-trichloro acetophenone is used in step 1. Brick red solid; yield 60%; $^1$H NMR (CD$_3$OD, 400 MHz): δ 10.07 (s, 1H), 8.89 (d, 1H, J=5.2 Hz), 8.45 (d, 1H, J=6.4 Hz), 7.98-7.92 (m, 2H), 7.83

(s, 1H), 7.76 (d, 1H, J=8.4 Hz), 7.50 (t, 1H, J=7.6 Hz); IR (KBr): $v_{max}$ 3453, 2924, 1637, 1508, 1070 cm$^{-1}$; MS (QQQ): m/z 339 [M−Cl]$^+$; HRMS: m/z 339.0093 calcd for $C_{18}H_9Cl_2N_2O^+$ (339.0086).

Example 5

Synthesis of 6-chloro-fascaplysin (5). Procedure of synthesis is similar to example number 1 (step 1, 2, and 3) except the respective starting material 2,6-dichloro acetophenone is used in step 1. Brick red solid; yield 65%; $^1$H NMR (CD$_3$OD, 400 MHz): δ 9.41 (d, 1H, J=5.6 Hz), 8.99 (d, 1H, J=5.6 Hz), 8.5 (d, 1H, J=8 Hz), 8.33 (d, 1H, J=8 Hz), 7.96-7.83 (m, 2H), 7.74 (d, 1H, J=8 Hz), 7.57 (d, 1H, J=7.2 Hz), 7.53 (d, 1H, J=8 Hz); $^{13}$C NMR (100 MHz, CD$_3$OD, ppm): δ 180.4 (CO), 149.7 (C), 149.0 (C), 138.7 (CH), 136.0 (CH), 135.0 (C), 133.9 (CH), 132.0 (C), 127.4 (CH), 125.2 (CH), 124.7 (CH), 124.0 (C), 123.0 (C), 122.0 (C), 121.1 (CH), 115.2 (CH), 114.7 (CH); IR (KBr): $v_{max}$ 3460, 2925, 1637, 1510, 1020 cm$^{-1}$; MS (Q-TOF): 305.0[M-F]$^+$; HRMS: m/z 305.0480 calcd for $C_{18}H_{10}ClN_2O^+$ (305.0476).

Example 6

Synthesis of 4,5-difluoro-fascaplysin (6). Procedure of synthesis is similar to example number 1 (step 1, 2, and 3) except the respective starting material 2-chloro, 4,5-difluoro acetophenone is used in step 1. Brick red solid; yield 60%; $^1$H NMR (CD$_3$OD, 400 MHz): δ 9.23 (d, 1H, J=12 Hz), 8.87 (s, 1H), 8.59 (d, 1H, J=8 Hz), 8.43-8.27 (m, 1H), 7.98-7.89 (m, 1H), 7.80-7.70 (m, 1H), 7.64 (d, 1H, J=8 Hz), 7.47-7.39 (m, 1H); IR (KBr): $v_{max}$ 3467, 2825, 1638, 1509, 1087 cm$^{-1}$; MS (Q-TOF): m/z 307 [M−Cl]$^+$; HRMS: m/z 307.0679 calcd for $C_{18}H_9F_2N_2O^+$ (307.0677).

Example 7

Synthesis of 5-chloro-fascaplysin (7). Procedure of synthesis is similar to example number 1 (step 1, 2, and 3) except the respective starting material 2,5-dichloro acetophenone is used in step 1. Brick red solid; yield 63%; $^1$H NMR (CD$_3$OD, 400 MHz): δ 9.26 (s, 1H), 8.88 (s, 1H), 8.40 (d, 1H, J=8 Hz), 7.98-7.80 (m, 3H), 7.72 (d, 1H, J=8 Hz), 7.44 (t, 1H, J=8 Hz); IR (KBr): $v_{max}$ 3468, 2964, 1637, 1417, 1020 cm$^{-1}$; MS (Q-TOF): m/z 305 [M−Cl]$^+$; HRMS: m/z 305.0478 calcd for $C_{18}H_{10}ClN_2O^+$ (305.0476).

Example 8

Synthesis of 1-benzoyl-9,N-dimethyl beta-carbolinium iodide (8).
Step 1: Procedure of synthesis is similar to example number 1 (step 1) except the respective starting material acetophenone is used in step 1.
Step 2: Procedure of synthesis is similar to example number 1 (step 2)
Step 3: A mixture of compound 41 (0.1 g, 1 mmol), methyl iodide (2 ml) and 1 ml DMF was heated for 12 h at 80° C. in sealed tube. The mixture was allowed to cool at 25° C. Compound was recrystallized with dichloromethane to yield compound 8 as yellow solid. Yield: 62%; $^1$H NMR (CD$_3$OD, 400 MHz): δ 8.74 (d, 1H, J=6.4 Hz), 8.61 (d, 1H, J=6.4 Hz), 8.40 (d, 1H, J=8 Hz), 7.91 (dd, 2H, J=1.2 & 1.2 Hz), 7.77-7.71 (m, 2H), 7.59-7.54 (m, 3H), 7.42 (t, 1H, J=7.2 Hz), 4.25 (s, 3H), 3.11 (s, 3H); $^{13}$C NMR (100 MHz, CD$_3$OD, ppm): δ 188.4 (CO), 146.8 (C), 137.9 (CH), 136.8 (C), 136.6 (CH), 136.31 (C), 135.7 (C), 134.9 (CH), 131.7 (CH), 131.1 (CH), 124.6 (CH), 123.7 (CH), 120.8 (C), 119.4 (CH), 114.0 (CH), 56.0 (CH$_3$), 46.6 (CH$_3$); IR (KBr): $v_{max}$ 3467, 2985, 2063, 1671, 1593, 1201, 1019 cm$^{-1}$; MS (ESI): m/z 301 [M−I]$^+$; HRMS: m/z 301.1335 calcd for $C_{20}H_{17}N_2O^+$ (301.1335).

Example 9

Synthesis of 1-(2-chloro-benzoyl)-9, N,N-dimethyl beta-carbolinium iodide (9). Procedure of synthesis is similar to example number 8 except the corresponding starting material 2-chloroacetophenone is used in step 1. Yellow solid; yield 60%; $^1$H NMR (CD$_3$OD, 400 MHz): δ 8.57 (d, 1H, J=6.4 Hz), 8.40 (d, 1H, J=6.4 Hz), 8.33 (dd, 1H, J=0.4 & 0.4 Hz), 7.75-7.66 (m, 2H), 7.40-7.37 (m, 3H), 7.31-7.27 (m, 1H), 4.43 (s, 3H), 3.21 (s, 3H); $^{13}$C NMR (100 MHz, CD$_3$OD, ppm): δ 187.1 (CO), 146.8 (C), 137.9 (CH), 137.4 (C), 136.6 (CH), 136.2 (C), 135.4 (C), 135.1 (C), 134.9 (C), 134.5 (CH), 134.4 (CH), 133.1 (CH), 129.7 (CH), 124.6 (CH), 123.8 (CH), 120.8 (C), 119.8 (CH), 114.1 (CH), 56.0 (CH$_3$), 35.4 (CH$_3$); IR (KBr): $v_{max}$ 3459, 2925, 1630, 1586, 1226, 1042 cm$^{-1}$; MS (ESI): m/z 335 [M−I]$^+$; HRMS: m/z 335.0942 calcd for $C_{20}H_{16}ClN_2O^+$ (335.0942).

Example 12

Synthesis of 1-(3-indoloyl)-9,N-dimethyl beta-carbolinium iodide (10). Procedure of synthesis is similar to example number 8 except the respective starting material 3-acetyl indole is used in step 1. Yellow solid; yield 65%; $^1$H NMR (DMSO-d6, 400 MHz): δ 12.72 (brs, NH), 8.97 (d, 1H, J=4.0 Hz), 8.87 (d, 1H, J=8.0 Hz), 8.58 (d, 1H, J=8.0 Hz), 8.42 (s, 1H), 8.17 (s, 1H), 7.83-7.79 (1H, t, J=8 Hz), 7.66-7.64 (t, 2H, J=4.0 Hz), 7.52-7.43 (m. 3H), 4.37 (s, 3H), 3.12 (s, 3H); $^{13}$C NMR (100 MHz, DMSO-d$_6$, ppm): δ 178.3 (CO), 40.87 (CH), 137.6 (c), 136.3 (c), 135.0 (CH), 134.4 (C), 133.0 (C), 132.3 (CH), 125.2 (C), 124.5 (CH), 123.6 (CH), 123.5 (CH), 123.4 (CH), 121.8 (CH), 119.2 (C), 117.8 (CH), 115.9 (C), 113.0 (10H), 54.4 (3CH), 45.2 (3CH), 34.4 (3CH); IR (KBr): $v_{max}$ 3467, 3419, 2930, 2855, 2427, 1634, 1618, 1584, 1457, 1248, 882 cm$^{-1}$; MS (Q-TOF): m/z 341 [M−I]$^+$.

Example 13

Synthesis of 1-(2-bromo-benzoyl)-9,N-dimethyl beta-carbolinium iodide (11). Procedure of synthesis is similar to example number 8 except the corresponding starting material 2-bromoacetophenone is used in step 1. Yellow solid; yield 65%; $^1$H NMR (CD$_3$OD, 400 MHz): δ 8.75 (d, 1H, J=4.0 Hz), 8.58 (d, 1H, J=8.0 Hz), 8.39 (dd, 1H, J=0.4, 0.4 Hz), 7.95-7.93 (m, 1H), 7.80-7.73 (m, 3H), 7.63-7.59 (m, 2H), 7.43 (t, 1H, J=8.0 Hz), 4.22 (s, 3H), 3.10 (s, 3H); IR (KBr): $v_{max}$ 3467, 2926, 2057, 1628, 1581, 1226, 1034 cm$^{-1}$; ESI-MS: m/z 381 [M−I]$^+$; HRMS: m/z 381.0487 calcd for $C_{20}H_{16}BrN_2O^+$ (379.0440).

Example 14

Synthesis of 1-(4-trifluoromethyl-benzoyl)-9,N-dimethyl beta-carbolinium iodide (12). Procedure of synthesis is similar to example number 8 except the respective starting material 4-trifluoroacetophenone is used in step 1. Yellow solid; yield 60%; $^1$H NMR (CD$_3$OD, 400 MHz): δ 8.57 (d, 1H, J=8.0 Hz), 8.40 (d, 1H, J=8.0 Hz), 8.34-8.32 (m, 1H), 8.09 (d, 2H, J=8 Hz), 7.75-7.66 (m, 4H), 7.45-7.37 (m, 1H), 4.44 (s, 3H); IR (KBr): $v_{max}$ 3453, 2926, 2063, 1633, 1413, 1278, 1064 cm$^{-1}$; ESI-MS: m/z 369 [M–I]$^+$.

Example 15

Synthesis of 1-(2-fluoro-benzoyl)-9,N-dimethyl beta-carbolinium iodide (13). Procedure of synthesis is similar to example number 8 except the respective starting material 2-fluoroacetophenone is used in step 1. yellow solid; yield 60%; $^1$H NMR (CD$_3$OD, 400 MHz): δ 8.73 (d, 1H, J=8.0 Hz), 8.59 (d, 1H, J=8.0 Hz), 8.39 (dd, 1H, J=0.4 & 0.4 Hz), 8.09-8.05 (m, 1H), 7.84-7.70 (m, 1H), 7.76-7.72 (m, 1H), 7.58 (d, 1H, J=8 Hz), 7.47-7.41 (m, 2H), 7.28-7.23 (m, 1H), 4.30 (s, 3H); $^{13}$C NMR (100 MHz, CD$_3$OD, ppm): δ 184.6 (CO), 164.5 (C), 163.1 (C), 146.7 (C), 142.0 (C), 140.4 (CH), 136.1 (CH), 134.4 (CH), 133.2 (CH), 127.2 (10H), 124.6 (CH), 123.8 (CH), 120.8 (C), 119.4 (CH), 118.7 (C), 118.5 (C), 114.0 (CH), 46.4 (CH$_3$); IR (KBr): $v_{max}$ 3453, 2956, 2073, 1632, 1520, 1163 cm$^{-1}$; ESI-MS: m/z 319 [M–I]$^+$.

Example 16

P-glycoprotein-induction assay. All synthesized compounds were screened for their ability to induce P-glycoprotein by using rhodamine123 (Rh123) cell exclusion method. In this method, the P-glycoprotein function was evaluated in terms of rhodamine 123 (Rh123) accumulation and efflux. Briefly, the protocol used is as follows: Colorectal LS180 cells Colorectal LS-180 cells [obtained from ECACC (European Collection of Cell Cultures) catalogue number: 87021202; passage number 52] were seeded at a density of 2×10$^4$ per well of 96 well plate and were allowed to grow for next 24 h. Cells were further incubated with the test compounds, and were diluted to a final concentration of 100 nM and rifampicin (standard) to a final concentration of 10 μM in complete media for 48 h. The final concentration of DMSO was kept at 0.1%. Drugs were removed and cells were incubated with HANKS buffer for 40 minutes before further incubation with HANKS buffer (containing 10 μM of Rh123 as a P-glycoprotein substrate) for 90 minutes. At the end of Rh123 treatment cells were washed four times with cold PBS followed by cell lysis for 1 h by using 200 μl of lysis buffer (0.1% Triton X-100 and 0.2 N NaOH). A total of 100 μl of lysate was used for reading fluorescence of Rh123 at 485 nm/529 nm Samples were normalized by dividing fluorescence of each sample with total protein present in the lysate. The Pgp-induction activity was measured in terms of the % intracellular accumulation of rhodamine 123/total protein inside LS180 cells. The decrease in the % intracellular accumulation (compared to control) of Rh123 indicates induction of P-glycoprotein as shown in Table 1. Rifampicin (10 μM) was used as a reference P-glycoprotein inducer. Statistical comparisons were made between control vs compounds by using Bonferroni test. The p value <0.5 was considered to be significant. P value *<0.5, <0.01, *<0.001.

TABLE 1

Pgp-induction activity of N-substituted β-carbolinium compounds in LS-180 cells.

| Entry | % Rh123 accumulation in LS-180 cells after 48 h$^a$ |
|---|---|
| Control | 100 |
| Rifampicin | 67.1 ± 4.6*** |
| 2 | 57.1 ± 9.2*** |
| 3 | 55.5 ± 6.9*** |

TABLE 1-continued

Pgp-induction activity of N-substituted β-carbolinium compounds in LS-180 cells.

| Entry | % Rh123 accumulation in LS-180 cells after 48 h$^a$ |
|---|---|
| 4 | 57.8 ± 8.3*** |
| 5 | 59.2 ± 6.7*** |
| 6 | 49.6 ± 1.2*** |
| 7 | 58.7 ± 7.8*** |
| 8 | 75.2 ± 9.1** |
| 9 | 71.4 ± 8.4** |
| 10 | 77.6 ± 7.6** |
| 11 | 70.1 ± 6.7** |
| 12 | 78.5 ± 5.8** |
| 13 | 79.0 ± 6.0** |

$^a$Pgp induction activity of compounds was checked at 5 μM; and was measured in terms of the % intracellular accumulation of rhodamine 123/total protein (μg) inside LS-180 cells.

The decrease in % intracellular accumulation (compared to control) of Rh123 indicates induction of Pgp. Rifampicin (10 μM) was used as a reference Pgp inducer.

Example 17

EC$_{50}$ determination in p-glycoprotein-induction assay. The experimental protocol was exactly similar as described above in example number 16. For EC$_{50}$ determination, different concentrations of compound were used to treat LS180 cells for 48 h. EC$_{50}$ was determined by plotting fluorescence of Rh123 against concentration of compound. Compounds 1 and 6 showed promising induction of P-glycoprotein with EC$_{50}$ values of 2.8 and 2.0 nM. The EC$_{50}$ results are shown in Table 2.

TABLE 2

Pgp induction activity in terms of EC$_{50}$ values of 1, 6 and 11

| Compound | Pgp induction EC$_{50}$ value |
|---|---|
| 1 | 2.8 nM |
| 6 | 2.0 nM |
| 11 | 3.0 nM |

Example 18

Western blot analysis. Protein was measured employing Bio-Rad protein assay kit using bovine serum albumin as standard. Proteins aliquots (70 μg) were resolved on SDS-PAGE and then electro transferred to PVDF membrane overnight at 4° C. at 30V. Nonspecific binding was blocked by incubation with 5% non-fat milk in Tris-buffered saline containing 0.1% Tween-20 (TBST) for 1 h at 25° C. The blots were probed with anti-P-glycoprotein antibody for 4 h and washed three times with TBST. Blot was then incubated with horseradish peroxidase conjugated antimouse secondary antibody for 1 h, washed again three times with TBST and signals detected using ECL plus chemiluminescence's kit on BioRad ChemiDoc XRS system. The Western-blot results are shown in FIG. 4. The increase in the density of Pgp in comparison to control indicates Pgp-induction activity. These results indicated that compound 11 possesses better Pgp induction activity than fascaplysin (1).

Example 19

Determination of thermodynamic equilibrium solubility. The compounds were first dissolved in methanol to prepare stock solutions (100 and 1000 µg/mL) Different concentrations of stock solutions were pipetted into the 96-well plates and the solvent was evaporated to ensure that solid drug was present in the beginning of the experiment. Thereafter, 200 µl of the dissolution medium (water) was added to the wells and 96-well plate was shaken horizontally at 300 rpm (Eppendorf Thermoblock Adapter, North America) for 4 h at room temperature (25±1° C.). The plates were kept overnight for equilibration of drug in medium. Later, the plates were centrifuged at 3000 rpm for 15 min (Jouan centrifuge BR4i). Supernatant (50 µl) was pipetted into UV 96-well plates (Corning® 96 Well Clear Flat Bottom UV-Transparent Microplate) for analyses with plate reader (SpectraMax Plus384) at $\lambda_{max}$ of 350 nm. The analyses were performed in triplicate for each compound. The solubility curve of concentration (µg/mL) vs absorbance was plotted to find out saturation point and the corresponding concentration was noted. The solubility of fascaplysin (1) and compounds 6 and 11 was determined. All three compounds showed optimum water solubility (>800 µg/ml).

TABLE 3

Solubility of N-substituted beta-carbolinium compounds 1, 6 and 11 in water, phosphate buffer saline (PBS), simulated gastric fluid (SGF), and simulated intestinal fluid (SIF).

| Compound | Solubility in µg/ml | | | |
|---|---|---|---|---|
| | Water | PBS | SGF | SIF |
| 1 | >1500 | >1500 | >1500 | >1500 |
| 6 | >1500 | 80 | 80 | <5 |
| 11 | 800 | nd | nd | nd | nd: not determined

ADVANTAGES OF THE INVENTION

The main advantages of the present invention are:
Compounds of the invention show promising P-glycoprotein induction activity at low nanomolar concentrations.
Compounds of the invention are stable.
Compounds of the invention are water-soluble.

We claim:
1. A compound represented by general formula A

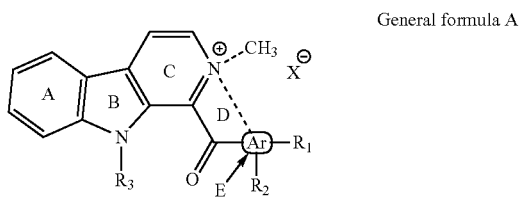

General formula A wherein, D ring may be cyclized or in open form,
when D ring is cyclized, the dotted line indicates a single bond connected from ortho-position of aromatic ring E (Ar) to the nitrogen atom of ring C, making a five-membered ring, wherein another dotted bond shown on nitrogen of C ring is not present;
when D ring is open, the dotted line connecting aromatic ring E (Ar) to the nitrogen atom of ring C indicates no bond, wherein another dotted bond shown on nitrogen of ring C indicates presence of single bond connecting nitrogen atom to the methyl group;

wherein, $R_1$ and $R_2$ groups are selected from halogens or trifluoromethyl; $R_3$ group is selected from hydrogen or methyl; X is selected from halogens; and Ar is selected from aryl and heteroaryl; and
$R_1$ and $R_2$ groups may be attached to any position on ring E.

2. A compound represented by formulae I or II,

Formulae I or II

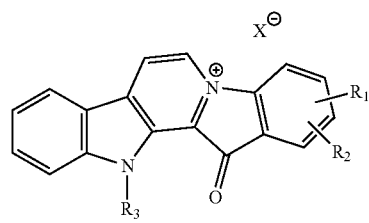

I

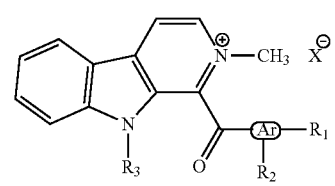

II wherein, $R_1$ and $R_2$ groups are selected from halogens or trifluoromethyl; $R_3$ group is selected from hydrogen or methyl; X is selected from halogens; and Ar is selected from aryl and heteroaryl; and
wherein, $R_1$ and $R_2$ groups may be attached to any position of aryl or heteroarayl ring;

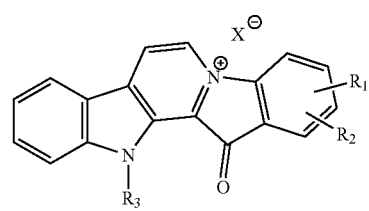

I

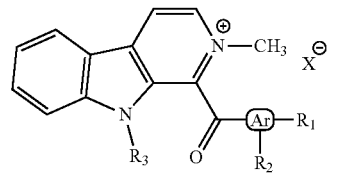

II

3. The compound as claimed in claim 1, wherein the compound is one selected from the group consisting of:

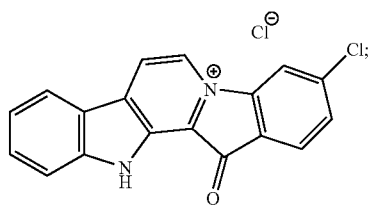

2

-continued

3

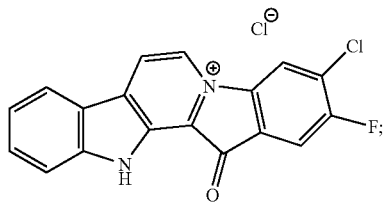

4

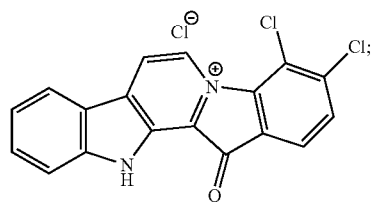

5

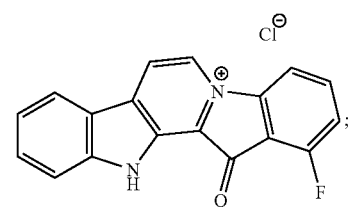

6

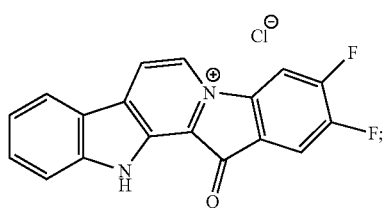

7

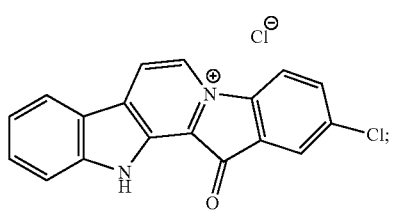

9

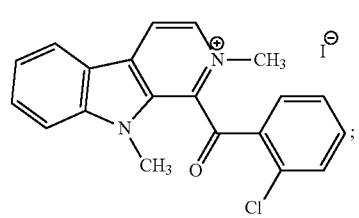

11

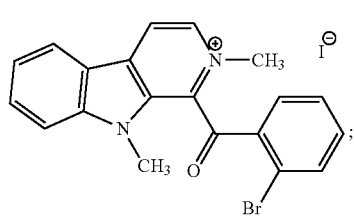

-continued

12

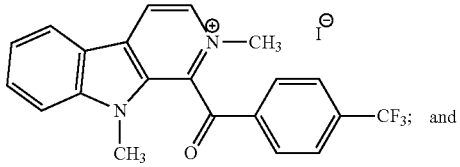

and

13

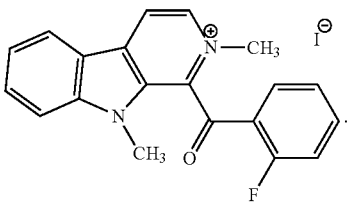

4. A process for the preparation of the beta-carbolinium compounds (2-13) as claimed in claim 3, wherein a) reacting tryptamine and substituted glyoxals in glacial acetic acid in presence of Pd/C catalyst at reflux temperature over a period of time ranging between 3 to 4 h;

b) furthermore, filtering the reaction mixture through filter paper and the filtrate was concentrated on rotary evaporator to get crude product which on silica gel column chromatography (10 to 20% ethyl acetate in hexane) gave β-carbolines;

c) heating the substituted benzoylated beta-carbolines as obtained in step b at a temperature ranging between 220-230° C. for a period of time ranging 15-20 minutes leads to cyclized beta carbolinium compounds, recrystallized from DCM/diethyl ether to obtain pure compound (2-7);

d) reacting substituted benzoylated beta carbolines as obtained in step b with the methyl iodide in DMF for a period of time ranging between 10 to 12 h at temperature ranging between 80 to 90° C. in sealed tube, wherein cooling of reaction mixture and recrystallization of reaction mixture from DCM provide pure compounds 9, 11-13.

5. A pharmaceutical composition comprising an effective amount of the compound of general formula A as claimed in claim 1 optionally along with the pharmaceutically acceptable excipients and diluents.

6. A pharmaceutical composition comprising an effective amount of the compound of formulae I or II as claimed as in claim 2 optionally along with the pharmaceutically acceptable excipients and diluents.

7. A composition as claimed in claim 5, wherein the pharmaceutically acceptable excipient is selected from the group consisting of saccharides, stearates, polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates, and talc.

8. The compound as claimed in claim 2, wherein the compound is one selected from the group consisting of:

2
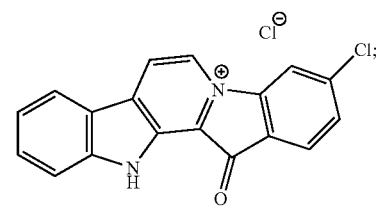
3
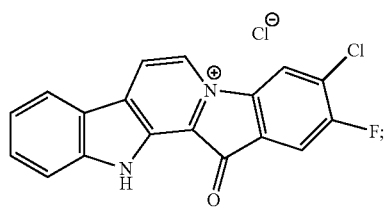
4
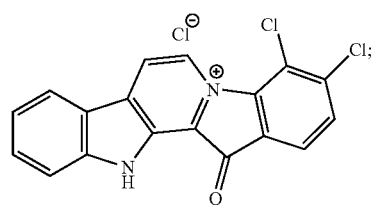
5
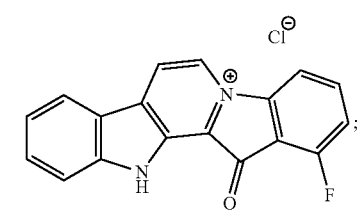
6
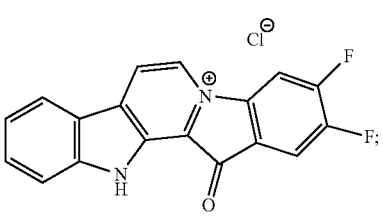
7
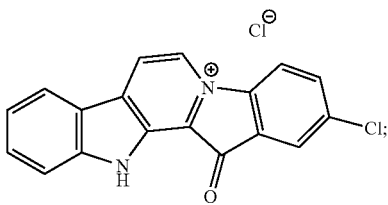
9
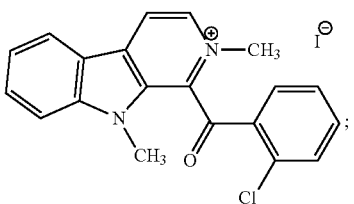
11
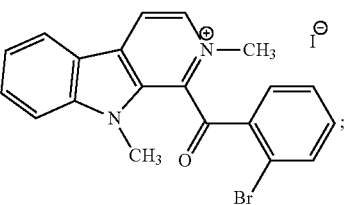
12
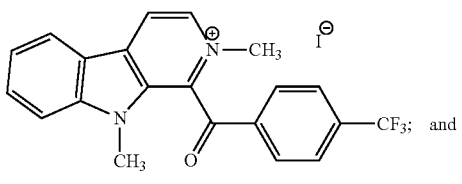
13
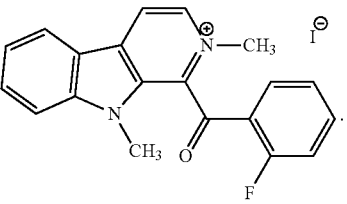
9. A composition as claimed in claim 6, wherein the pharmaceutically acceptable excipient is selected from the group consisting of saccharides, stearates, polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates, and talc.
* * * * *